(12) United States Patent
Dor et al.

(10) Patent No.: US 9,280,738 B2
(45) Date of Patent: Mar. 8, 2016

(54) IDENTIFICATION TAG AND ATTACHMENT

(71) Applicant: HALDOR ADVANCED TECHNOLOGIES LTD, Hod HaSharon (IL)

(72) Inventors: Guy Dor, Rosh-Haayn (IL); Morr Avissara, Shoham (IL)

(73) Assignee: HALDOR ADVANCED TECHNOLOGIES LTD, Hod Hasharon (IL)

( * ) Notice: Subject to any disclaimer, the term of this patent is extended or adjusted under 35 U.S.C. 154(b) by 16 days.

(21) Appl. No.: 14/269,155

(22) Filed: May 4, 2014

(65) Prior Publication Data

US 2015/0317555 A1    Nov. 5, 2015

(51) Int. Cl.
*G06K 19/06* (2006.01)
*G06K 19/077* (2006.01)
*G06K 19/04* (2006.01)

(52) U.S. Cl.
CPC .......... *G06K 19/07758* (2013.01); *G06K 19/04* (2013.01); *Y10T 29/49018* (2015.01)

(58) Field of Classification Search
CPC ............ G06K 19/07749; G06K 17/00; G06K 7/10693; G06K 13/08; G07F 7/1008; B42D 15/10; B41M 3/144; G06Q 10/087; G06Q 10/08
USPC ..................... 235/492, 487, 491, 462.13, 385
See application file for complete search history.

(56) References Cited

U.S. PATENT DOCUMENTS

| | | | |
|---|---|---|---|
| 6,450,402 B1 | 9/2002 | Regev | |
| 7,837,694 B2 | 11/2010 | Tethrake et al. | |
| 7,887,559 B2 | 2/2011 | Deng et al. | |
| 2008/0177267 A1* | 7/2008 | Sands et al. ..................... | 606/80 |
| 2008/0238677 A1 | 10/2008 | Blair | |
| 2013/0321129 A1 | 12/2013 | Swenson, Jr. et al. | |
| 2014/0048605 A1* | 2/2014 | Gatling et al. ................ | 235/492 |

FOREIGN PATENT DOCUMENTS

| | | |
|---|---|---|
| DE | 19807264 C2 | 10/2000 |
| WO | 2010065688 | 6/2010 |
| WO | 2012146867 | 11/2012 |
| WO | 2013020944 | 2/2013 |

OTHER PUBLICATIONS http://www.xerafy.com/en/catalogue/product/pico-on-plus/4 Pico-On Plus.
http://www.xerafy.com/blog/tracking-surgical-instruments-rfid/ Tracking Surgical Instruments With RFID.

* cited by examiner

*Primary Examiner* — Karl D Frech
(74) *Attorney, Agent, or Firm* — Soroker-Agmon

(57) ABSTRACT

An identification tag for attaching to a tool to automatically identify the tool, including, a base with a small footprint for attaching to the tool on one end of the base, an identification attachment with a larger footprint that is attached to the tool by the base at a second end of the base. Wherein the identification attachment includes, an encasement that is connected to the second end of the base, an identification circuit that fits into the encasement, a cover to seal the encasement, and wherein the identification circuit accepts communication queries and transmits identification information related to the tool wirelessly from within the encasement.

17 Claims, 6 Drawing Sheets

IDENTIFICATION TAG AND ATTACHMENT

TECHNICAL FIELD

The present invention relates to the attachment of identification tags to small objects and tools.

BACKGROUND

There are many environments in which multiple tools and disposables are used, including for example operation rooms, aircraft hangars, garages, or the like.

An operation room is a facility in which intrusive operations are performed on patients. Typically, multiple people participate in an operation, including a chief surgeon, sometimes an assistant surgeon, an anesthesiologist, a scrub nurse, and a circulating nurse. The participating personnel members use multiple tools, such as scalpels, forceps, and others, varying according to the surgery being performed.

Intensive efforts are invested in keeping track of all tools and disposables, in order to make sure no tool unintentionally remains inside the patient's body. Therefore careful counting is performed before, during and after the operation.

Counting the tools is a tedious job and requires intensive resources, including mental resources, personnel time and down-time of the operating room. Counting the tools towards the end of an operation also increases the time the patient's body is open with the associated risks.

In addition, counting is not always error-free, and in many cases tools end up being left within the patient's body, causing severe damage and even death.

Another problem relates to the life cycle of tools. For example, the tools used in an operation have to be sanitized or sterilized prior to further usage. Other constraints may relate to maintenance operations required for the tools, for example, a blade may have to be sharpened after every predetermined number of operations in which it is used. In another example, tools that have been used in an operation performed on a patient with a contagious disease may require extra sterilization before further usage, or the like. Making sure that each tool is used and maintained properly also imposes expenses and requires resources, including record keeping and tracking, manual labor and the like.

It would be useful to use a computerized system for counting and keeping track of the tools and their maintenance. Such a system needs to uniquely identify each tool. In U.S. Pat. No. 8,193,938 to Halberthal et al dated Jun. 5, 2012 there is disclosed a system and method for keeping track of tools. Identifying tools is performed using a Radio Frequency (RF) identification transducer tag that is attached to the tools.

Attaching such tags to tools imposes a number of challenges. The tag needs to adhere to the tool for the entire lifetime of the tool, the tag should not interfere with the use of the tool, the tag should be identifiable regardless of the orientation of the tool and even when surrounded by other tools of similar type.

SUMMARY

An aspect of an embodiment of the disclosure relates to an identification tag for automatically identifying a tool. The identification tag includes a base with a small footprint for attaching the identification tag to the tool, and an identification attachment attached to the other end of the base, the identification attachment has a footprint that is larger than the footprint of the base. The identification attachment includes an identification circuit that accepts wireless communication queries and responds with identification information for identifying the tool. Optionally, the identification information may be a unique identifier or it may include details related to the tool, for example manufacture date, serial number or other information.

There is thus provided according to an exemplary embodiment of the disclosure, an identification tag for attaching to a tool to automatically identify the tool, comprising:

a base with a small footprint for attaching to the tool on one end of the base;

an identification attachment with a larger footprint that is attached to the tool by the base at a second end of the base;

wherein said identification attachment comprises:

an encasement that is connected to the second end of the base;

an identification circuit that fits into the encasement;

a cover to seal the encasement; and wherein the identification circuit accepts communication queries and transmits identification information related to the tool wirelessly from within the encasement.

In an exemplary embodiment of the disclosure, the base and the tool are made from the same material family. Optionally, the base is attached to the tool by a laser welding process. Alternatively, the base is attached to the tool by an ultra-sonic process.

In an exemplary embodiment of the disclosure, the identification information is preprogrammed to include the manufacture date of the attached tool. Optionally, the cover is sealed by an ultra-sonic process. In an exemplary embodiment of the disclosure, the encasement is shaped like a cylindrical cup. Optionally, the size of the footprint of the identification attachment is at least double the size of the footprint of the base. In an exemplary embodiment of the disclosure, the second end of the base includes two arms extending from the base and forming an arc. Optionally, one side of the arms has jagged teeth.

There is further provided according to an exemplary embodiment of the disclosure, a method of forming an identification tag to identify a tool, comprising:

attaching one end of a base with a small footprint to a selected position on the tool;

coupling a second end of the base to an identification attachment;

wherein said identification attachment comprises:

an encasement that is connected to the second end of the base;

an identification circuit that fits into the encasement;

a cover to seal the encasement; and wherein the identification circuit accepts communication queries and transmits identification information related to the tool wirelessly from within the encasement.

In an exemplary embodiment of the disclosure, the base is made from the same material family as the tool. Optionally, the base is attached to the tool by a laser welding process. Alternatively, the base is attached to the tool by an ultra-sonic process. In an exemplary embodiment of the disclosure, the cover is sealed by an ultra-sonic process. Optionally, the encasement is shaped like a cylindrical cup.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
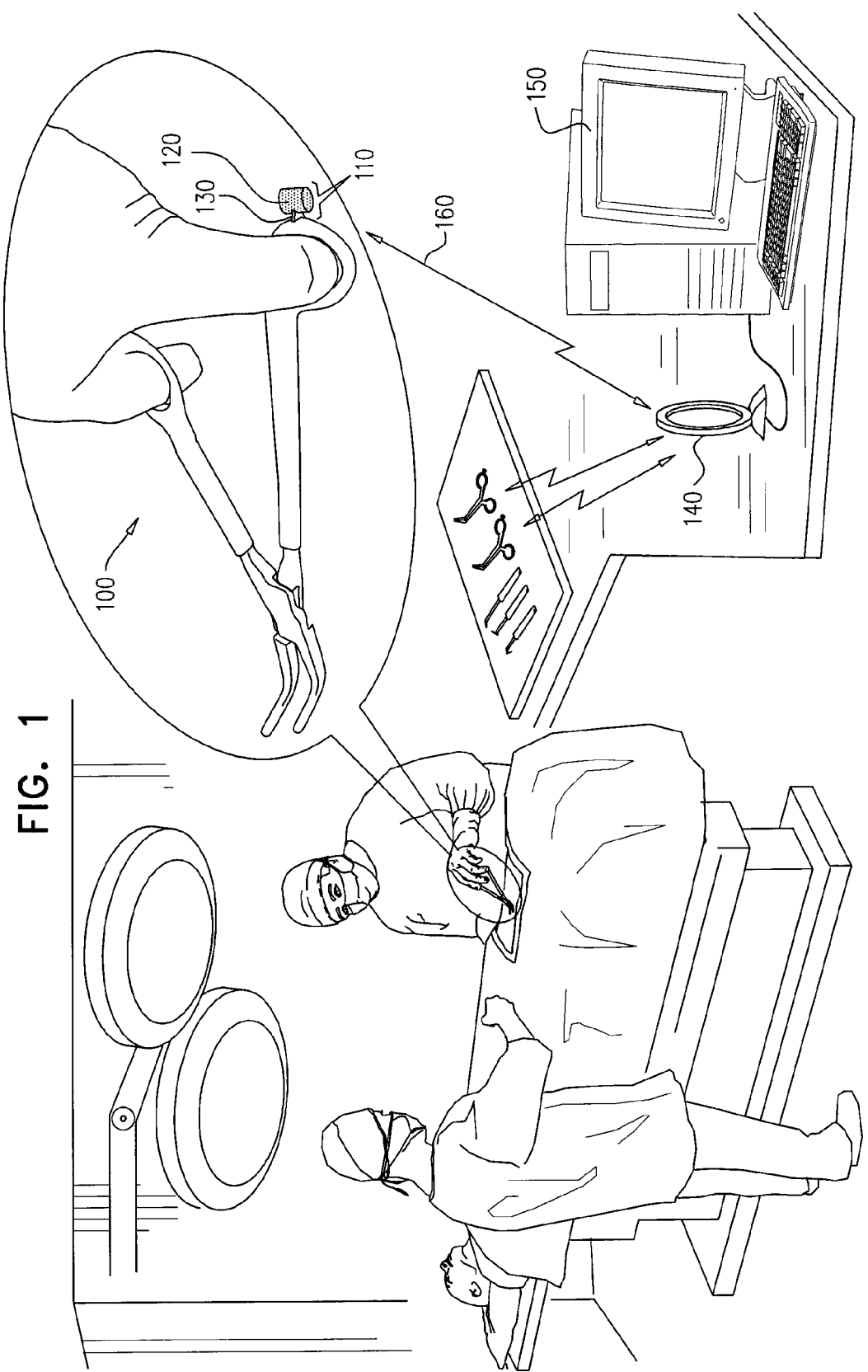
FIG. 1 is a schematic illustration of a tool with an identification tag, according to an exemplary embodiment of the disclosure.

FIG. 1 is a schematic illustration of a tool 100 with an identification tag 110, according to an exemplary embodiment of the disclosure. Identification tag 110 includes an identification attachment 120 that is connected to the tool 100 with a base 130 serving as an interface between the tool 100 and the identification attachment 120. In an exemplary embodiment of the disclosure, the base 130 has a small footprint relative to tool 100 and relative to identification attachment 120, so that it can be attached to tool 100 even if only a small area is available for attaching base 130. Optionally, the size of the footprint of base 130 may be 3 mm by 3 mm, 2 mm by 2 mm or less. In contrast identification attachment 120 may have a footprint of about 6 mm by 3 mm or more thus covering an area of more than twice the size of the footprint of base 130. This enables use of larger identification attachments 120 with only a small attachment area on the tool 100. Additionally, a small attachment area allows quicker attachment. In a typical implementation, the attachment area is between 1-2 mm by 1-2 mm and the size of identification attachment 120 is about 5-9 mm by 3-5 mm.

In an exemplary embodiment of the disclosure, base 130 is made from the same or similar material as tool 100 or at least as the same material at the point of attachment on the tool, for example if the tool 100 is made from a metal the base 130 is also made from a metal (e.g. both from stainless steel, titanium etc.). Likewise if the tool is made from a polymer also the base may be made from a polymer. Optionally, this allows treating tool 100 with the identification attachment 120 in the same manner as before the attachment, for example sterilizing, heating and the like. In an exemplary embodiment of the disclosure, the same material may mean the same material family, for example both made from metal, both made from a polymer or both made from a similar metal although not identical.

In an exemplary embodiment of the disclosure, metal tools and metal bases will be attached using a laser welding process, whereas polymer tools and polymer bases will be attached using an ultra-sonic process. Alternatively, other attachment processes may be used.

In an exemplary embodiment of the disclosure, identification attachment 120 is an RFID tag that provides a unique identifier. Optionally, during use one or more antennas 140 are positioned in the vicinity of tools 100. The antennas are capable of reading the unique identifiers by communicating (160) with identification attachments 120 and transmitting the identity of the identified tool to a computer 150. Optionally, computer 150 keeps track of the identity of the identified tools 100, the time of identifying, the location of the tools 100 (or identity of the antenna 140 that located the identification attachment 120). In an exemplary embodiment of the disclosure, based on the recorded information computer 150 can keep track of the tools as they are moved from one location to another.

In an exemplary embodiment of the disclosure, FIGS. 2-6 illustrate a method of manufacturing and attaching identification tags 110 for use in tracking tools.

Figure 2:
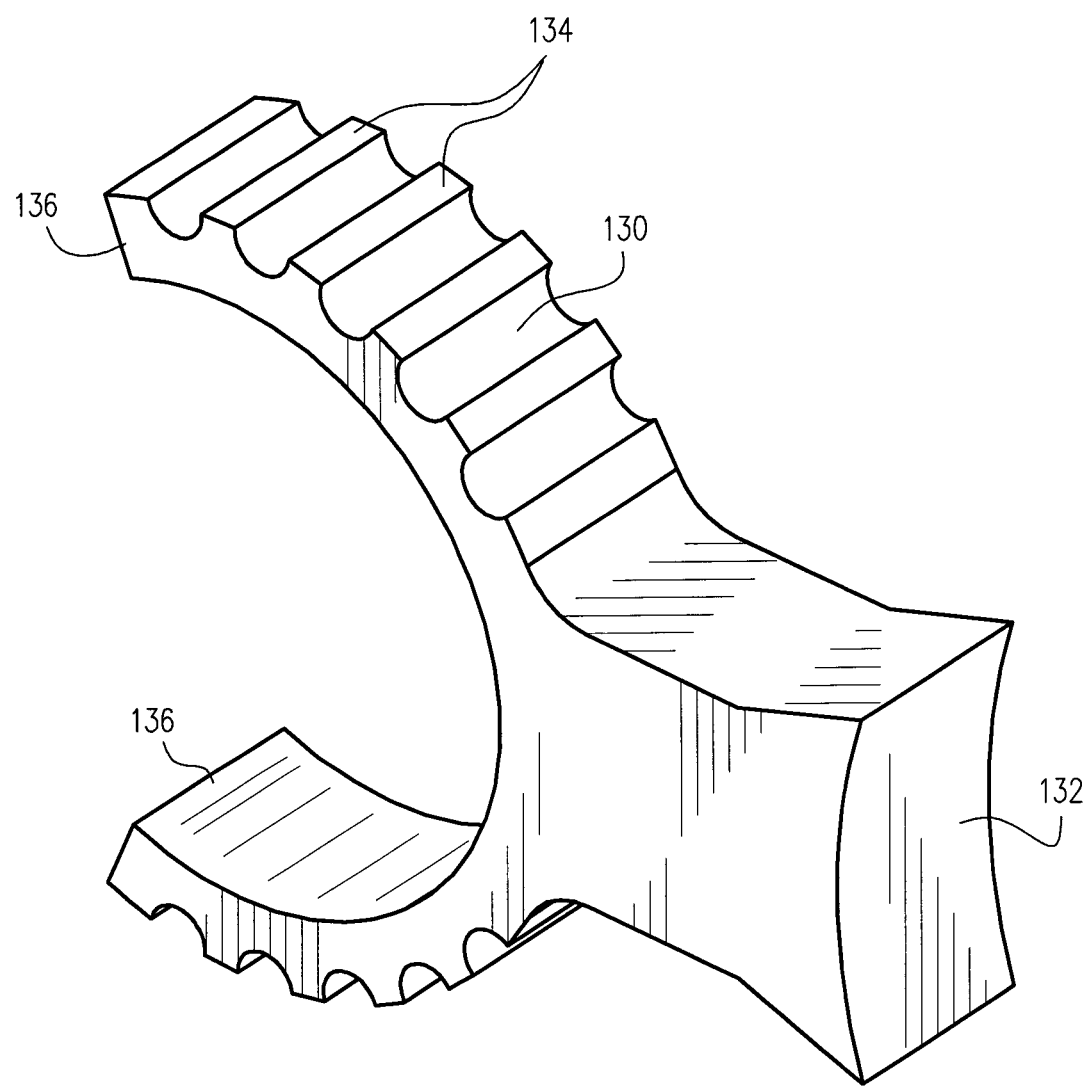
FIG. 2 is a schematic illustration of a base for attaching an identification attachment of an identification tag to a tool, according to an exemplary embodiment of the disclosure.

FIG. 2 is a schematic illustration of base 130 for attaching identification tag 110 to a tool 100, according to an exemplary embodiment of the disclosure. In an exemplary embodiment of the disclosure, base 130 includes a bottom 132, which is essentially flat or slightly curved for coupling with tool 100. Optionally, on the other end base 130 includes 2 arms 136 that extend outward forming an arc to hold base 130 in place once an encasement is formed around it as explained below. In some embodiments of the disclosure, at least one side of arms 136 are formed with jagged teeth 134 to enhance the grip of base 130 in the encasement.

Figure 3A:
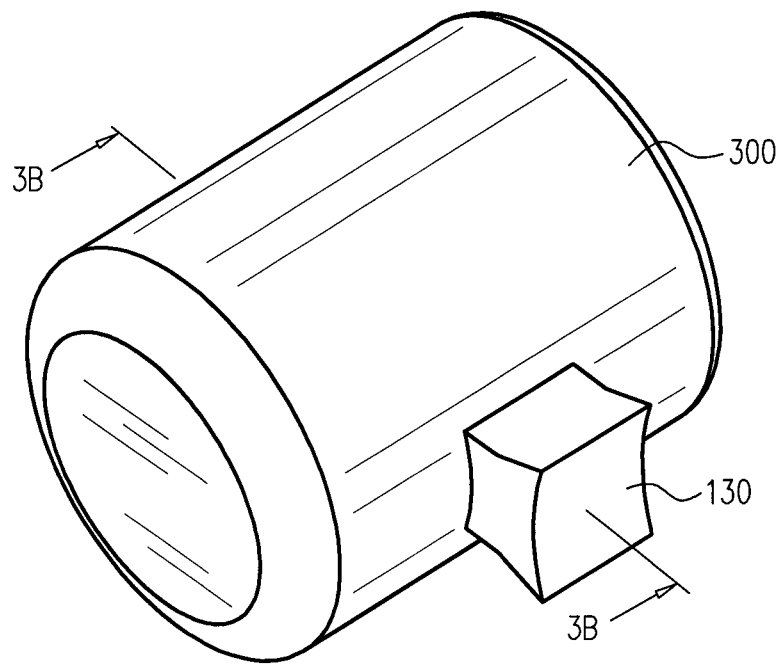
FIGS. 3A and 3B are schematic illustrations of an encasement for holding an identification circuit of an identification tag, according to an exemplary embodiment of the disclosure.
Figure 3B:
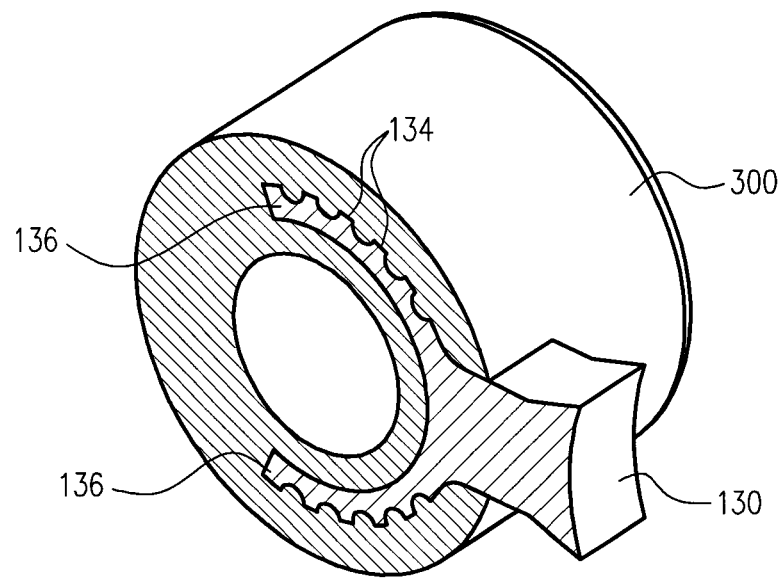

FIGS. 3A and 3B (cross sectional view) are schematic illustrations of an encasement 300 for holding an identification circuit 500 (FIG. 5) of identification attachment 120, according to an exemplary embodiment of the disclosure. Optionally, encasement 300 is formed by an over mold process using a polymer material over base 130 forming a cylindrical cup like structure with base 130 serving as an interface to attach the encasement 300 to tool 100. Optionally, encasement 300 serves to protect identification circuit 500, which will be sealed inside the encasement. Alternatively, the encasement may be constructed mechanically to surround and/or grasp base 130.

Figure 4:
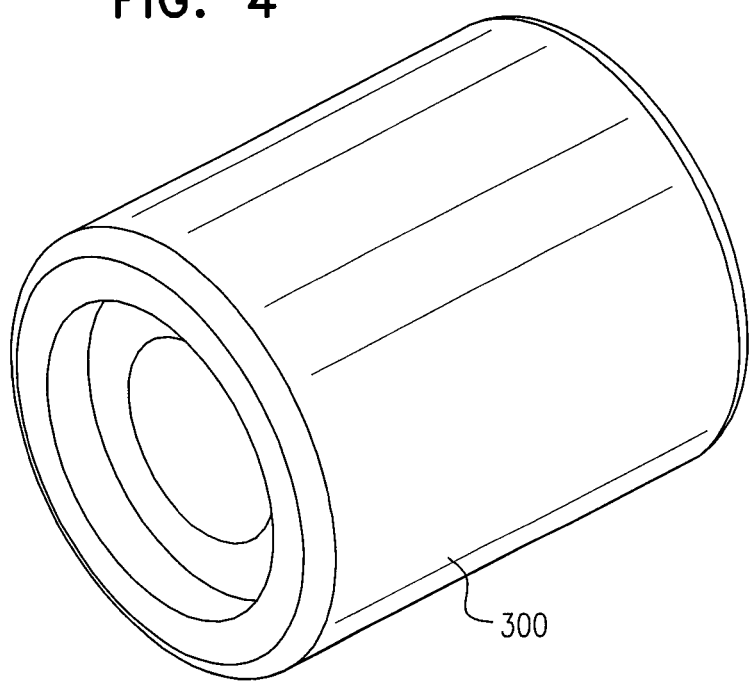
FIG. 4 is a schematic illustration of a side view of an encasement for holding an identification circuit of an identification tag, according to an exemplary embodiment of the disclosure.

FIG. 4 is a schematic illustration of a side view of encasement 300 for holding identification circuit 500 of identification attachment 120, according to an exemplary embodiment of the disclosure. As can be seen in FIG. 4 the over mold process produces a cup like structure with a cylindrical void for inserting identification circuit 500.

Figure 5A:
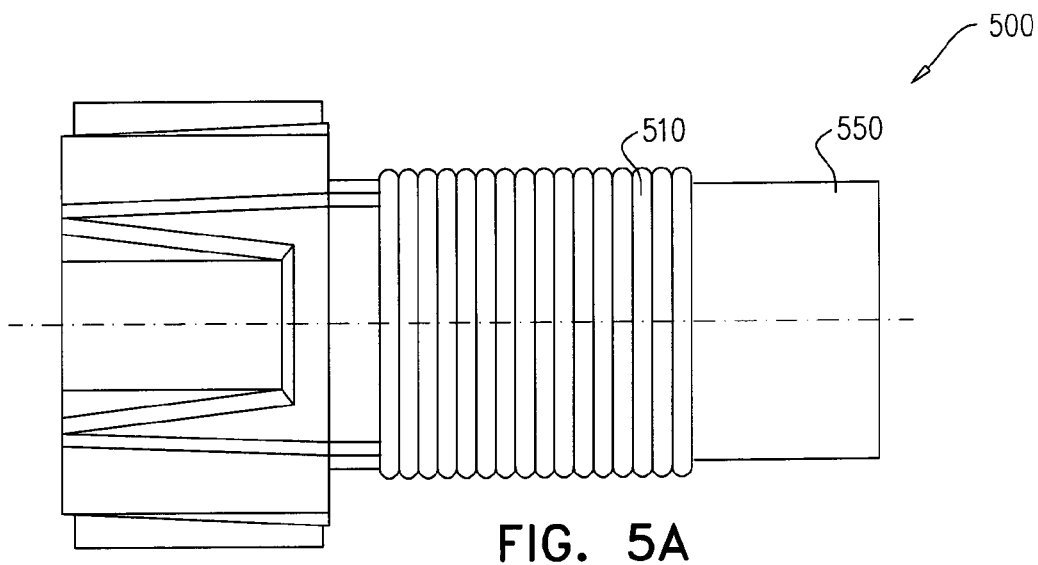
FIGS. 5A, 5B and 5C are schematic illustration of an identification circuit, according to an exemplary embodiment of the disclosure.
Figure 5B:
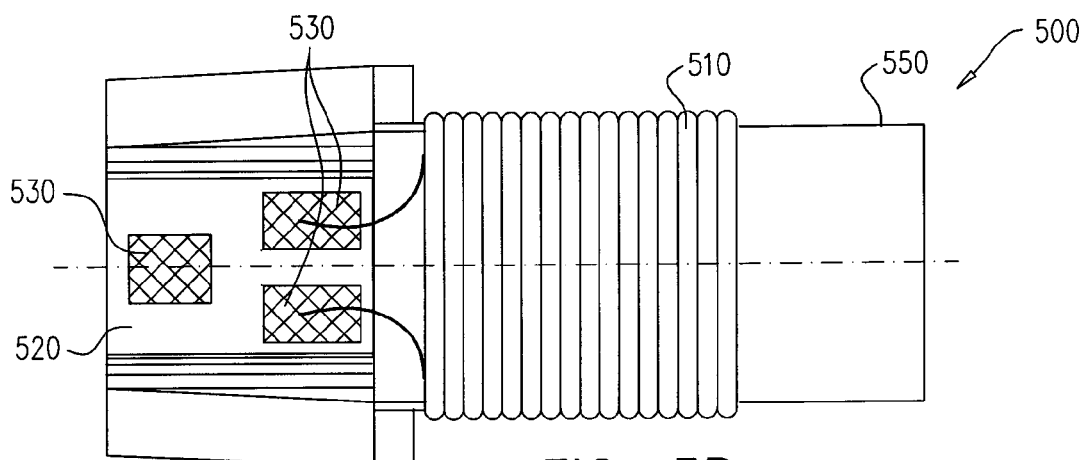
Figure 5C:
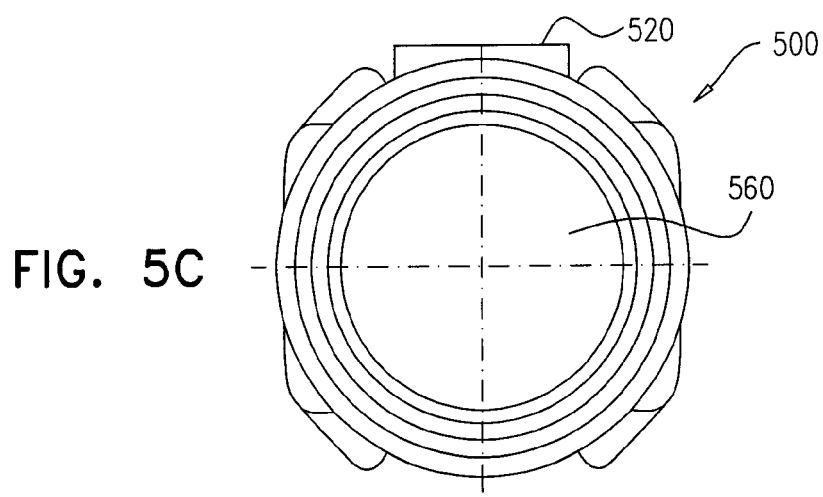

FIGS. 5A, 5B and 5C are schematic illustrations of identification circuit 500 from 3 orthogonal perspectives (A, B, C), according to an exemplary embodiment of the disclosure. Optionally, identification circuit 500 is an RFID circuit that returns a unique identification value when queried by an antenna 140 (as shown in FIG. 1). In some embodiments of the disclosure, identification circuit may also store information about the tool it is attached to, for example a count value related to the number of times the tool underwent a specific process (e.g. sterilization). Alternatively, computer 150 may keep track of such information based on the unique ID value. In some embodiments of the disclosure, the unique ID may include an owner ID, a serial no, product number, manufacturing date, batch number, manufacturing location and other information either of the identification circuit or of the tool 100 that it is attached to. Optionally, the chip may be pre-programmed with the information from computer 150 when attached to the tool or may be manufactured to be attached when the tool is manufactured. In FIG. 5 orientation C shows a side view of the identification circuit 500, orientation B shows a top view and orientation A shows a bottom view.

In an exemplary embodiment of the disclosure, identification circuit 500 includes a ferrite core 550 with a coil 510 wrapped around it to send and receive electromagnetic signals. Optionally, ferrite core 550 is cylindrical to enhance reception in multiple directions. In an exemplary embodiment of the disclosure, identification circuit 500 includes a chip 520 with contacts 530. As shown in FIG. 5 (C) the coil is connected to contacts 530 so that the chip 520 may communicate. In some embodiments of the disclosure, identification circuit 560 may include a battery 560 to transmit with a strong signal, although identification circuit 500 may rely on the received signals for the power to respond.

Figure 6:
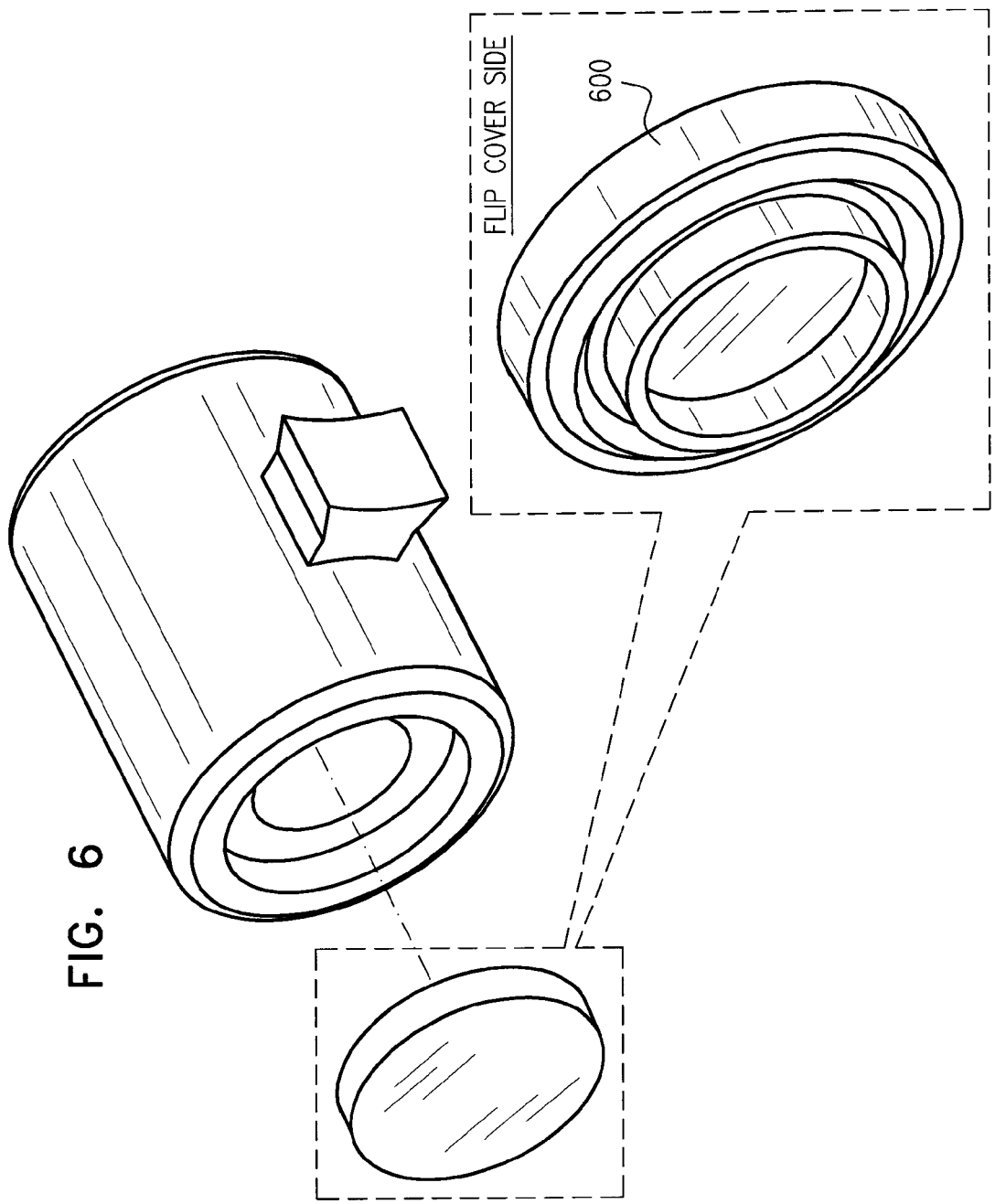
FIG. 6 is a schematic illustration of a cover for sealing an encasement of an identification tag, according to an exemplary embodiment of the disclosure.

In an exemplary embodiment of the disclosure, identification circuit 500 is inserted into the cylindrical void shown in FIG. 4 so that it will be protected by encasement 300. FIG. 6 is a schematic illustration of a cover 600 for sealing encasement 300, according to an exemplary embodiment of the disclosure. Optionally, cover 600 is placed over encasement 300 and sealed by an ultra-sonic process, by heating or by mechanical means. Once encasement 300 is sealed identification circuit 500 is protected from moisture, gases (oxidation) and other external influences, so that identification circuit 500 will be able to serve for the entire life of tool 100. Optionally, identification attachment 120 is compatible with sterilization processes such as steam, ETO (Ethylene Oxide), No2 (Nitrogen Dioxide), Plasma (Hydrogen Peroxide). Additionally, identification attachment 120 does not interfere with the functionality of the tool 100.

In an exemplary embodiment of the disclosure, multiple identification attachments 120 may be identified simultaneously. Additionally, in contrast to flat RFID tags identification attachment 120 is identifiable almost in any direction and less subject to interference by other identification attachments 120 blocking reception of transmissions from antennas 140.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove.

We claim:

1. An identification tag for attaching to a tool to automatically identify the tool, comprising:
    a base with a small footprint for attaching to the tool on one end of the base;
    an identification attachment with a larger footprint that is attached to the tool by said base at a second end of the base;
    wherein said identification attachment comprises:
        an encasement that is connected to the second end of said base;
        an identification circuit that fits into said encasement;
        a cover to seal the encasement; and
        wherein the identification circuit accepts communication queries and transmits identification information related to the tool wirelessly from within the encasement.

2. An identification tag according to claim 1, wherein the base and the tool are made from the same material family.

3. An identification tag according to claim 1, wherein the base is attached to the tool by a laser welding process.

4. An identification tag according to claim 1, wherein the base is attached to the tool by an ultra-sonic process.

5. An identification tag according to claim 1, wherein the identification information is preprogrammed to include manufacturing information of the attached tool.

6. An identification tag according to claim 1, wherein the cover is sealed by an ultra-sonic process.

7. An identification tag according to claim 1, wherein the encasement is shaped like a cylindrical cup.

8. An identification tag according to claim 1, wherein the size of the footprint of the identification attachment is at least double the size of the footprint of the base.

9. An identification tag according to claim 1, wherein the second end of the base includes two arms extending from the base and forming an arc.

10. An identification tag according to claim 9, wherein one side of the arms has jagged teeth.

11. An identification tag according to claim 1, wherein the encasement is formed as an over-mold over the base.

12. A method of forming an identification tag to identify a tool, comprising:
    attaching one end of a base with a small footprint to a selected position on the tool;
    coupling a second end of the base to an identification attachment;
    wherein said identification attachment comprises:
        an encasement that is connected to the second end of said base;
        an identification circuit that fits into said encasement;
        a cover to seal the encasement; and
        wherein the identification circuit accepts communication queries and transmits identification information related to the tool wirelessly from within the encasement.

13. A method according to claim 12, wherein said base is made from the same material family as the tool.

14. A method according to claim 12, wherein the base is attached to the tool by a laser welding process.

15. A method according to claim 12, wherein the base is attached to the tool by an ultra-sonic process.

16. A method according to claim 12, wherein the cover is sealed by an ultra-sonic process.

17. A method according to claim 12, wherein the encasement is shaped like a cylindrical cup.

* * * * *